US009171537B2

(12) United States Patent
Davidson et al.

(10) Patent No.: US 9,171,537 B2
(45) Date of Patent: Oct. 27, 2015

(54) APPARATUS AND METHOD FOR CANCELLING, REDUCING AND MODULATING NOISE SIGNAL AND FOR SIGNAL ENHANCING AND SIGNAL PROOFING

(75) Inventors: Lance Samuel Davidson, Scottsdale, AZ (US); Dennis Lee Edwards, Scottsdale, AZ (US)

(73) Assignee: UNR, LLC, Scottsdale, AZ (US)

( * ) Notice: Subject to any disclaimer, the term of this patent is extended or adjusted under 35 U.S.C. 154(b) by 962 days.

(21) Appl. No.: 12/636,709

(22) Filed: Dec. 12, 2009

(65) Prior Publication Data

US 2010/0150366 A1 Jun. 17, 2010

Related U.S. Application Data

(60) Provisional application No. 61/201,558, filed on Dec. 12, 2008.

(51) Int. Cl.

*H03B 29/00* (2006.01)
*G10K 11/16* (2006.01)
*A61F 11/06* (2006.01)
*G10K 11/178* (2006.01)
*H04R 1/10* (2006.01)

(52) U.S. Cl.

CPC ........ *G10K 11/178* (2013.01); *G10K 2210/108* (2013.01); *G10K 2210/129* (2013.01); *H04R 1/1083* (2013.01)

(58) Field of Classification Search

CPC .......... G10K 11/178; G10K 2210/129; G10K 2210/108; G10K 11/1788; G10K 11/1784; H04R 1/1083

USPC ........... 381/71.1, 71.7, 71.8, 71.14, 123, 150, 381/122, 13, 94.1, 94.2, 94.7, 3; 327/551; 455/130, 570, 569.1, 501, 67.13, 114.2

See application file for complete search history.

(56) References Cited

U.S. PATENT DOCUMENTS

| | | | | | |
|---|---|---|---|---|---|
| 2,966,549 | A | * | 12/1960 | Fogel | 381/57 |
| 5,375,174 | A | * | 12/1994 | Denenberg | 381/71.6 |
| 5,600,471 | A | * | 2/1997 | Hirohashi et al. | 398/136 |
| 6,947,526 | B2 | * | 9/2005 | Wilson | 379/68 |
| 2007/0036367 | A1 | * | 2/2007 | Ko | 381/71.1 |

* cited by examiner

*Primary Examiner* — Vivian Chin
*Assistant Examiner* — Con P Tran
(74) *Attorney, Agent, or Firm* — Barry Choobin; Patent360 LLC

(57) ABSTRACT

The embodiments herein provide an apparatus and method for cancelling signal noise. According to one embodiment, an apparatus for cancelling signal noise has a sensor or receiver to capture the undesirable signals. A transducer converts the energy of the captured signals and modulates the captured undesirable signals. A signal inverting circuit is connected to the transducer to generate the inverse of the captured undesirable signals by inverting the amplitude of the undesirable signal while maintain the frequency at the same level. The generated inverse of the undesirable signal transmitted by a transmitter is received by a receiver and output through a speaker so that the output inverse of the undesirable signal is combined with the undesirable signal to produce a desired signal environment.

10 Claims, 4 Drawing Sheets

APPARATUS AND METHOD FOR CANCELLING, REDUCING AND MODULATING NOISE SIGNAL AND FOR SIGNAL ENHANCING AND SIGNAL PROOFING

CROSS REFERENCE TO RELATED APPLICATION

We claim benefit of an earlier filed Provisional Application with Application No. 61/201,558 which was filed on 12 Dec. 2008.

BACKGROUND OF INVENTION

1. Technical Field

The embodiments herein generally relate to noise signal reducing apparatus and methods and particularly to cancelling device and method for noise signals. More particularly the embodiments herein relate to an apparatus and method for cancelling, reducing, modulating, noise signals and for signal enhancement and signal-proofing with a wireless or wired apparatus.

2. Description of the Related Art

Often, the public, businessmen, the military and professionals endure constant, varying and distracting noise. Hence, environmental noise has become a very significant issue for many homes, businesses and other institutions. A variety of different factors contribute to the problem of environmental noise pollution. The different factors include increasing population density, per capita space reduction, and increasing levels of industrial, transportation and residential noise. Noise sources are increasingly perceived as environmental pollution and are considered to be a diminution of quality of life. Examples of the noise sources include but are not limited to roads and freeways, airplanes, industrial institutions, plants and factories, air conditioners and pool equipment, and many others.

Accordingly, it is desirable to have an apparatus for reducing the environmental noise and enable an individual to establish, on command, absolute or a desired level of silence. Further, it is desirable to have an apparatus and method to enable a person or persons to resist, exclude or modulate a variety of signals in a variety of locales. For example, a hotel room in a densely populated urban area could reduce traffic noise, a military debriefing room could be made 'secure,' and a classroom could be improved to avoid undesired stimuli that would otherwise distract learning students.

Hence, there is a need to provide an efficient system and method for cancelling, reducing, modulating, noise signals and for signal enhancement and signal-proofing with a wireless or wired apparatus.

The above-mentioned shortcomings, disadvantages and problems are addressed herein and will be understood by reading and studying the following specification.

SUMMARY OF THE INVENTION

The following presents a simplified summary of the invention in order to provide a basic understanding of some aspects of the invention. This summary is not an extensive overview of the invention. It is not intended to identify key/critical elements of the invention or to delineate the scope of the invention. Its sole purpose is to present some concept of the invention in a simplified form as a prelude to the more detailed description that is presented later.

The embodiments herein relate generally to, among other things, the fields of military and diplomatic intelligence gathering, and delivery of intelligence and misinformation; auditory and medical research; consumer appliances; business appliances; education; electronic technology; private and public auditoria for orchestras, theater, etc., and robot technology. The term "noise" wherever mentioned in the specification means an undesirable signal or signals. The term 'signal' is not limited to just sound waves, but also includes light particles, smell particles, touch/sensation signals, and taste signals.

The primary object of the embodiments herein is to provide an apparatus and methods for cancelling signal noise modulation, reduction, signal noise cancellation, signal enhancement, and signal-proofing.

Another object of the embodiments herein is to provide an efficient, practical, simple apparatus and/or methods to eliminate or significantly reduce undesirable signals.

Yet another object of the embodiments herein is to provide an efficient, practical, simple apparatus and/or methods to enhance signals, substitute signals, isolate signals and modulate signals.

Yet another object of the embodiments herein is to provide an efficient, practical, simple apparatus and/or methods that is operated irrespective of whether the apparatus is in proximity and/or remote to the subject.

Yet another object of the embodiments herein is to provide an efficient, practical, simple apparatus and/or methods that will transmit silencing descriptor information to a receiver or receivers for signal or noise cancellation.

The embodiments herein provide an apparatus and method for cancelling signal noise modulation, reduction, signal noise cancellation for signal noise modulation. Examples of the signal noise include, but are not limited to sound signal, light signal, smell signal touch or sensation signal and taste signal. According to one embodiment, an apparatus for cancelling signal noise has a means for capturing undesirable signals, especially from one area to another confined or open area. A transducer is connected to the means for capturing the undesirable signals for receiving the captured undesirable signals, for converting the energy of the captured signals and for modulating the captured undesirable signals. The sound waves in this embodiment are converted into analog signals. A signal-inverting circuit is connected to the transducer to generate the inverse of the captured undesirable signals. A means for transmitting is connected to the signal inverting circuit to transmit the output of the signal inverting circuit. A means for communications is provided to communicate the output of the signal inverting circuit transmitted using the means for transmitting. A means for receiving is provided to receive the inverted signal transmitted by the means for transmitting. A signal output device is connected to the means for receiving to output the inverted signal received by the means for receiving. A power source is provided to supply power to all the components in the apparatus.

The signal output device outputs the inverted signal received by the means for receiving to cancel the undesirable signal. The means for capturing the undesirable signal is a sensor or a receiver for detecting an undesirable signal. The sensor or receiver is automatically tuned to a specific frequency of the signal. The sensor or the receiver has a feature for adjusting the volume of the specific signal for achieving any desired degree of noise cancellation.

The signal inverting circuit generates a signal which is the inverse of the undesirable signal captured by the means for capturing. The output signal from the signal inverting circuit has an amplitude which is inverse of the captured, undesired signal and a frequency which is same as the frequency of the captured, undesired signal. The undesired signal is a signal selected from a group comprising noise, undesirable sounds, visual stimuli, touch stimuli and taste stimuli.

The means for communications is a wired network to communicate the output of the signal inverting circuit, which is transmitted using the means for transmitting. The means for communications is a wireless network to communicate the output of the signal inverting circuit, which is transmitted using the means for transmitting. The transmitted inverse of the captured undesirable signal is communicated through a fully or partially wireless network. The transmitted inverse of the captured undesirable signal is communicated through a partially wired or partially wireless network or optical communications system.

According to another embodiment, a method for cancelling signal noise is provided. The method involves capturing undesirable signals, generating inverse signals of the captured undesirable signal, transmitting the generated inverse of the captured undesirable signal, receiving the transmitted inverse of the captured undesirable signal and outputting the received inverse of the captured undesirable signal to cancel the undesirable signal.

The undesirable signals are captured using a sensor or receiver. The captured undesirable signal is passed through a signal inverting circuit to generate the inverse of the captured undesirable signal. The inverse signal has an amplitude which is inverse of the captured undesirable signal and a frequency which is same as the frequency of the captured undesirable signal. The undesired signal is a signal selected from a group comprising noise, undesirable sounds, visual stimuli, touch stimuli and taste stimuli.

The transmitted inverse of the captured undesirable signal is communicated through a wired network. The transmitted inverse of the captured undesirable signal is communicated through a fully or partially wireless network. The transmitted inverse of the captured undesirable signal is communicated through a partially wired or partially wireless network or optical communications system.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The embodiments herein will be better understood from the following detailed description with reference to the drawings, in which.

Figure 1:
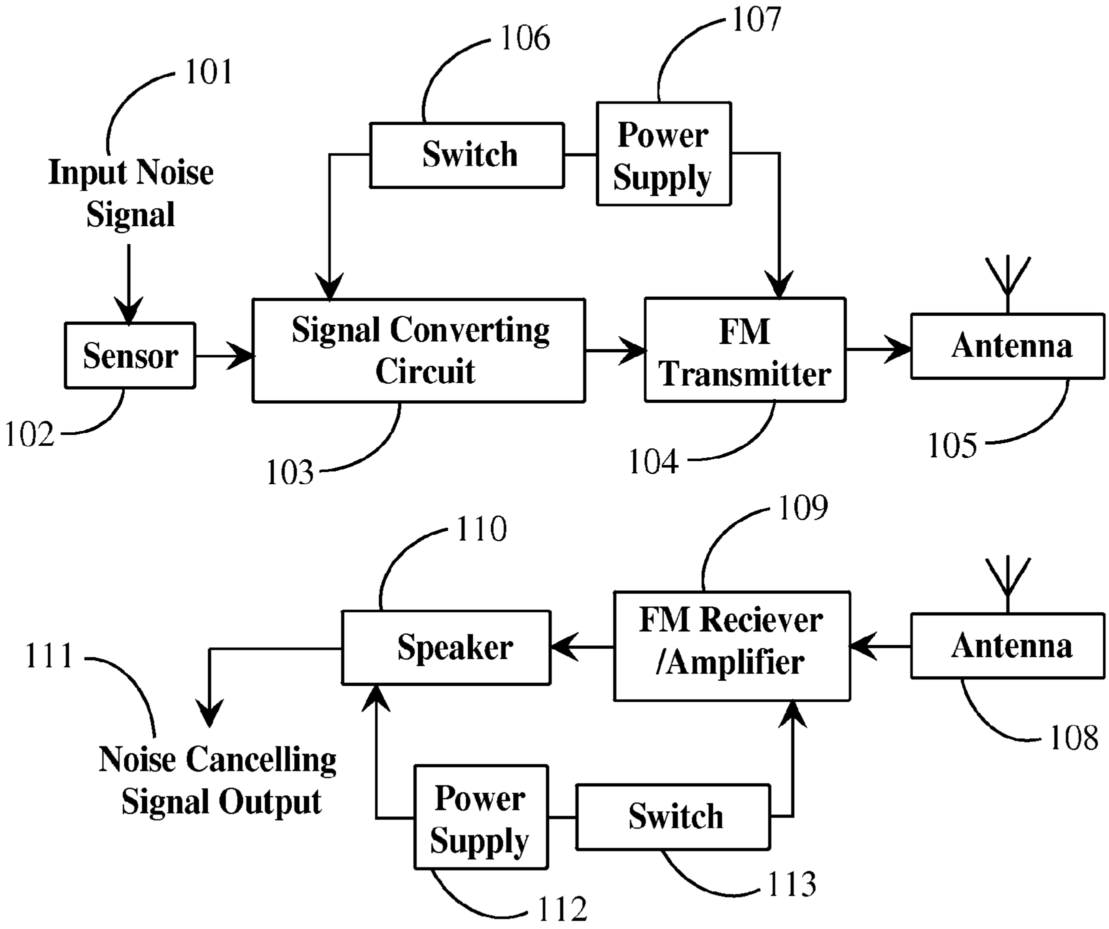
FIG. 1 illustrates a block circuit diagram of an apparatus for cancelling, reducing, modulating noise signal and for signal enhancing and signal proofing, according to one embodiment.

Although specific features of the present invention are shown in some drawings and not in others. This is done for convenience only as each feature may be combined with any or all of the other features in accordance with the present invention.

DETAILED DESCRIPTION

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

The embodiments herein provide an apparatus and method for cancelling signal noise modulation, reduction, signal noise cancellation for signal noise modulation. Examples of the signal noise include, but are not limited to sound signal, light signal, smell signal, touch or sensation signal and taste signal. According to one embodiment, an apparatus for cancelling signal noise has a means for capturing undesirable signals. A transducer is connected to the means for capturing the undesirable signals for receiving the captured undesirable signals, for converting the energy of the captured signals and for modulating the captured undesirable signals. A signal inverting circuit is connected to the transducer to generate the inverse of the captured undesirable signals. A means for transmitting is connected to the signal inverting circuit to transmit the output of the signal inverting circuit. A means for communications is provided to communicate the output of the signal inverting circuit transmitted using the means for transmitting. A means for receiving is provided to receive the inverted signal transmitted by the means for transmitting. A signal output device is connected to the means for receiving to output the inverted signal received by the means for receiving. A power source is provided to supply power to all the components in the apparatus.

The signal output device outputs the inverted signal received by the means for receiving to cancel the undesirable signal. The means for capturing the undesirable signal is a sensor or a receiver for detecting an undesirable signal. The sensor or receiver is automatically tuned to a specific frequency of the signal. The sensor or the receiver has a feature for adjusting the volume of the specific signal for achieving any desired degree of noise cancellation.

The signal inverting circuit generates a signal which is inverse of the undesirable signal captured by the means for capturing. The output signal from the signal inverting circuit has amplitude which is inverse of the captured, undesirable signal and a frequency which is same as the frequency of the captured, undesirable signal. The undesirable signal is a signal selected from a group comprising noise, undesirable sounds, visual stimuli, touch stimuli and taste stimuli.

The means for communications is a wired network to communicate the output of the signal inverting circuit, which is transmitted using the means for transmitting. The means for communications is a fully or partially wireless network to communicate the output of the signal inverting circuit, which is transmitted using the means for transmitting.

According to another embodiment, a method for cancelling signal noise is provided. The method involves capturing undesirable signals, generating inverse signals of the captured undesirable signal, transmitting the generated inverse of the captured undesirable signal, receiving the transmitted inverse of the captured undesirable signal and outputting the received inverse of the captured undesirable signal to cancel the undesirable signal.

The undesirable signals are captured using a sensor or receiver. The captured undesirable signal is passed through a signal inverting circuit to generate the inverse of the captured undesirable signal. The inverse signal has an amplitude which is the inverse of the captured undesirable signal and a frequency which is same as the frequency of the captured undesirable signal. The undesirable signal is a signal selected from a group comprising noise, undesirable sounds, visual stimuli, touch stimuli and taste stimuli.

The transmitted inverse of the captured undesirable signal is communicated through a wired network. The transmitted inverse of the captured undesirable signal is communicated through a fully or partially wireless network. The transmitted inverse of the captured undesirable signal is communicated through a partially wired or partially wireless network or optical communications system.

According to one embodiment, the sensor or a receiver is placed on or about a suction cup or other device attached to one or more windows to capture outside noise and transmit the signal to a stereo receiver in a house or office to create silence inside residential or commercial space, respectively. The apparatus cancels the signal noise by replicating or mirroring the signal so that the listener is unaware of the undesirable ambient sound and can instead focus on the desired sound.

The sensors and receivers have the ability to automatically tune to the specific frequency of the signal and modulate/adjust volume for any desired degree of noise cancellation or to be manually adjusted, remotely or otherwise. The sensors and receivers, transmitters and printed circuit boards are expected to be, but need not be, in a closed or partially closed, stationary or moving [e.g., a vehicle], space. The power source for the apparatus could be AC, DC, AC/DC, battery, solar or otherwise.

The apparatus and related components need not be separate or stand-alone. For example, a window or wall could contain within or could be embedded with the receivers, transmitters, power sources and printed circuit boards. The signals could be electromagnetic or otherwise, and need not be within sensory receptors to the human, e.g., audible to the human ear, observable to the human eye, etc. The term 'signal' is not limited to just sound signals, but also includes light signals, smell signals, touch/sensation signals and taste signals, etc.

FIG. 1 illustrates a block circuit diagram of an apparatus for cancelling, reducing, modulating noise signal and for signal enhancing and signal proofing, according to one embodiment. With respect to FIG. 1, sensor 102 is provided for capturing noise or undesirable signals 101. The undesirable signal is a signal selected from a group comprising noise, undesirable sounds, visual stimuli, touch stimuli and taste stimuli. The examples of the sensors include, but are not limited to, a condenser microphone for sensing a sound signal, a lens for sensing light signal and a pressure gauge for sensing touch or sensation signal. The sensed signal noise is passed to a signal inverting circuit 103 for inverting the sensed signal noise. The signal inverting circuit 103 inverts amplitude of the sensed signal noise without changing the frequency of the sensed signal noise. The signal inverting circuit 103 sends the inverted noise signal to a FM transmitter 104 provided with an antenna 105. The antenna 105 tuned to 88 MHz transmits the inverted signal noise to FM receiver 109 tuned to 88 MHz. A power supply 107 along with a switch 106 (ON/OFF modulating switch) is connected to the signal inverting circuit 103 and FM transmitter 104 to supply power during the entire process of generating and transmitting the inverted signal noise. Examples of the power supply 107 include, but are not limited to an Alternating Current (AC) source, a Direct Current (DC) source, a battery and a solar power source.

The FM receiver 109 receives the inverted signal noise through the antenna 108. The FM receiver 109 amplifies the inverted signal noise and sends the amplified inverted signal noise to a transducer such as a speaker 110. An example of the transducer 110 includes a speaker. The transducer such as speaker 110 outputs the amplified inverted noise signal 111 to the surrounding area so that the amplified inverted noise signal 111 combines with the signal noise 101 to reduce or eliminate or cancel the level of unwanted signal noise perceived by a listener. A power supply 112 along with a switch 113 (ON/OFF modulating switch) connected to the FM receiver 109 and transducer such as speaker 110 powers entire process of amplifying the inverted noise signal and producing the noise cancellation signal 111. Examples of the power supply 112 include, but are not limited to an Alternating Current (AC) source, a Direct Current (DC) source, a battery and a solar power source.

In various embodiments, the elements are populated on a Printed Circuit Board (PCB) to form a Printed Circuit Board Assembly (PCBA) for generating the noise cancellation signal 111 to cancel the signal noise so that the noise cancellation signal 111 combines with the signal noise 101 to reduce or eliminate the level of unwanted signal noise 111 perceived by a listener.

Figure 2:
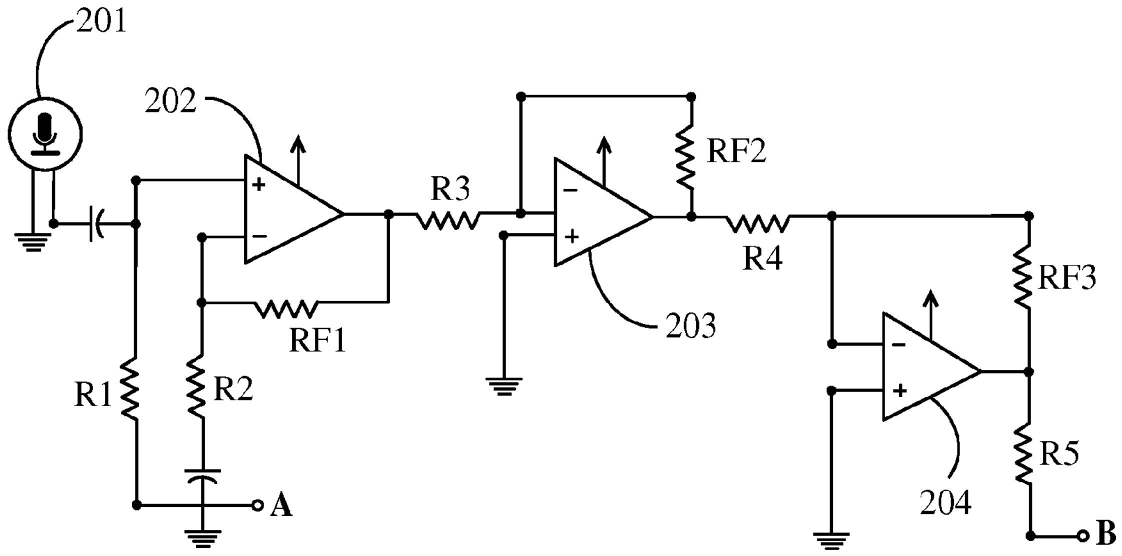
FIG. 2 is a block circuit diagram of a signal inverting circuit in an apparatus for cancelling, reducing, modulating noise signal and for signal enhancing and signal proofing, according to one embodiment.

FIG. 2 is a block circuit diagram of a signal inverting circuit in an apparatus for cancelling, reducing, modulating noise signal and for signal enhancing and signal proofing, according to one embodiment. With respect to FIG. 2, the signal noise inverting circuit includes a condenser microphone 201, a High Pass Filter (HPF) and three cascaded Operational Amplifiers (OPAMs) 202-204 in series to produce an inverted signal noise for reducing the signal noise originated in a surrounding area. The condenser microphone 201 is provided for sensing the signal noise (sound signal). The signal noise (sound signal) input to the microphone 201 is passed through the HPF which includes a capacitor C1 and resistor R1. The HPF offers easy passage of high frequency signal noise. The sensed high frequency signal noise is fed to the non-inverting input of the OPAMP 202. The inverting-input of the OPAMP 202 is grounded through a resistor R2 and a capacitor. A feedback resistor RF1 is connected from output of the OPAMP 202 to the inverting-input of the OPAMP 202 to provide a negative feedback. The OPAMP 202 inverts amplitude of the high frequency signal noise at first stage due to negative feedback provided through the resistance RF1.

The inverted high frequency signal noise output from the OPAMP 202 is fed to an OPAMP 203 through a resistance R3. Non inverting-input of the OPAMP 203 is grounded. A feedback resistor RF2 is connected from output of the OPAMP 203 to the inverting-input of the OPAMP 203. The OPAMP 203 inverts amplitude of the inverted high frequency signal noise received from the OPAMP 202 due to negative feedback provided through the resistance RF2. Further, the inverted high frequency signal noise output from the OPAMP 203 is fed to an OPAMP 204 through a resistance R4. Non inverting-input of the OPAMP 204 is grounded. A feedback resistor RF3 is connected from output of the OPAMP 204 to the inverting-input of the OPAMP 204. The OPAMP 204 inverts amplitude of the inverted high frequency signal noise received from the OPAMP 204 due to negative feedback provided through the resistance RF3. The inverted signal noise output from the OPAMP 204 forms the final output of the signal noise inverting circuit collected through load resistance R5.

Figure 3:
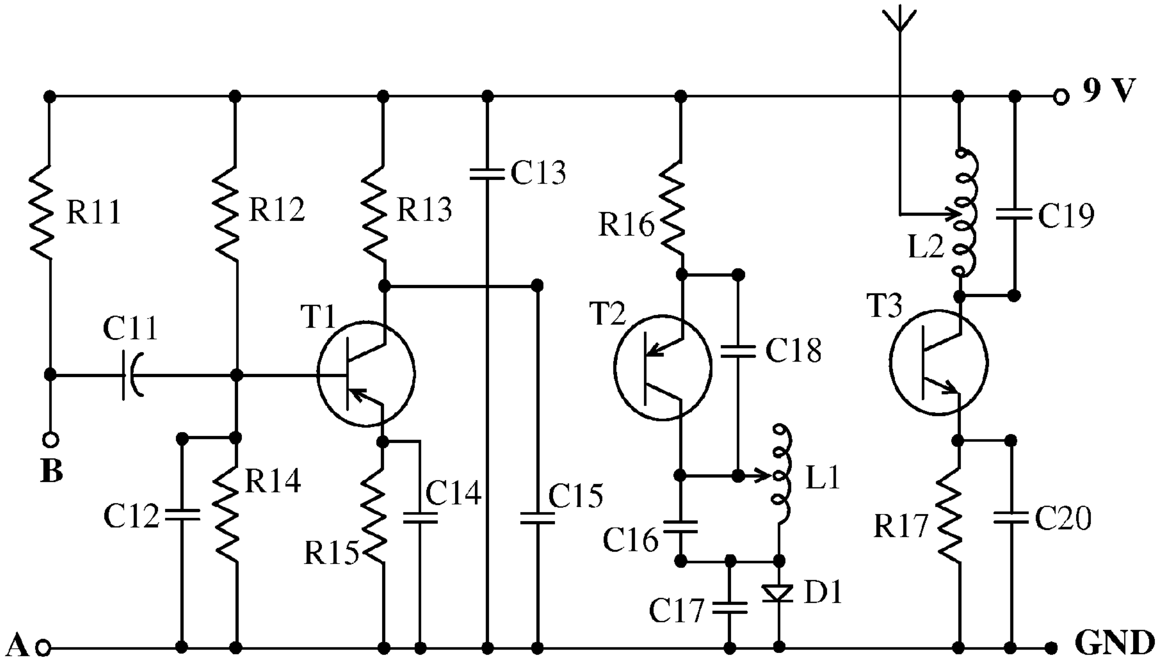
FIG. 3 is block circuit diagram of FM transmitter used in an apparatus for cancelling, reducing, modulating noise signal and for signal enhancing and signal proofing, according to one embodiment.

FIG. 3 is block circuit diagram of a FM transmitter used in an apparatus for cancelling, reducing, modulating noise signal and for signal enhancing and signal proofing, according to one embodiment. With respect to FIG. 3 an inverted anti-noise signal is fed to the FM transmitter. The FM transmitter transmits the inverted noise signal over a carrier wave by changing frequency of the inverted noise signal. The FM transmitter is provided with an oscillator to generate a carrier RF signal. Frequency modulation takes place at the oscillator stage. The frequency modulated signal is passed through filter and then finally amplified by a power amplifier, and finally delivered to an antenna provided in the FM transmitter. The FM transmitter radiates the FM inverted noise signal through the antenna provided in the FM transmitter. The radiated FM inverted noise signal is transmitted to an FM receiver.

Figure 4:
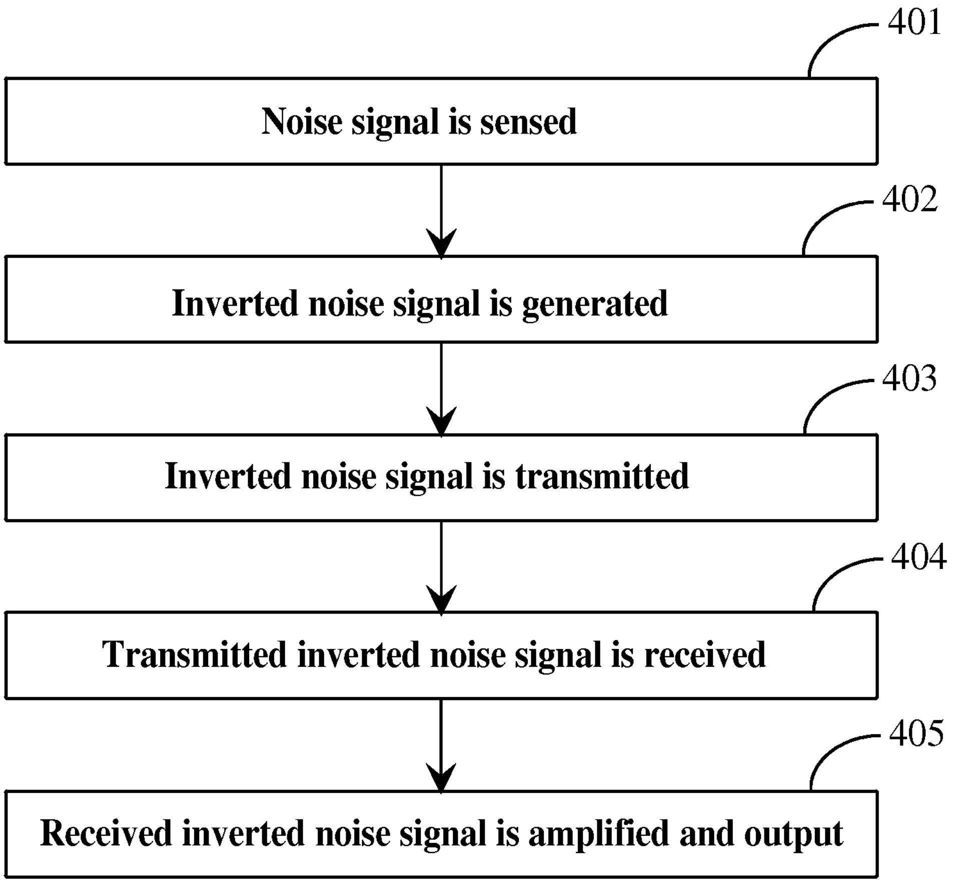
FIG. 4 is a flow chart illustrating a method for cancelling, reducing, modulating noise signal and for signal enhancing and signal proofing, according to one embodiment.

FIG. 4 is a flow chart illustrating a method for cancelling, reducing, modulating noise signal and for signal enhancing and signal proofing, according to one embodiment. A signal noise is sensed or captured by a sensor or receiver (401). An inverted noise signal is generated using a signal inverting circuit. Amplitude of the sensed signal noise is inverted while the frequency of the sensed signal noise maintained at the same level (402). The generated inverted noise signal is transmitted using a FM transmitter (403). The transmitted inverted noise signal is received by a FM receiver (404). The received inverted signal is amplified and output through a transducer such as a speaker so that the amplified inverted noise signal is combined with the input signal noise to reduce or eliminate or cancel the level of unwanted signal noise perceived by a listener (405). In various embodiments, the signal noise of an exterior environment is reduced in an interior space. The signal noise of interior space is reduced within the interior space, or the signal noise of an exterior environment is reduced in the exterior environment. Examples of the noise signal include, but are not limited to a sound signal, light signal, smell signal, touch or sensation signal and taste signal.

Although the invention is described with various specific embodiments, it will be obvious for a person skilled in the art to practice the invention with modifications. However, all such modifications are deemed to be within the scope of the claims.

It is also to be understood that the following claims are intended to cover all of the generic and specific features of the embodiments described herein and all the statements of the scope of the embodiments herein which as a matter of language might be said to fall there between.

What is claimed is:

1. An apparatus for cancelling signal noise comprising:

a means for capturing undesirable signals, and wherein the means for capturing undesirable signal is a sensor or a receiver for detecting an undesirable signal, and wherein the sensor or receiver is automatically tuned to the frequency of the undesirable signal;

a transducer for converting the energy of the captured undesirable signals;

a signal inverting circuit connected to the transducer, wherein the signal inverting circuit generates an output signal which is inverse of the undesirable signal captured by the means for capturing, and wherein the output signal from the signal inverting circuit has an amplitude which is amplitude of inverse captured, undesirable signal and a frequency which is same as the frequency of the captured, undesirable signal;

a means for transmitting connected to the signal inverting circuit to transmit the output of the signal inverting circuit, and wherein the means for transmitting is a frequency modulated (FM) transmitter;

a means for communication and wherein the means for communications is a partially wired and partially wireless network and wherein the means for communications is an optical communication network;

a means for receiving the output of the signal inverting circuit transmitted by the means for transmitting, and wherein the means for receiving is a FM receiver/amplifier;

a signal output device to output the signal received by the means for receiving, and wherein the output signal cancels the signal noise;

a power supply and wherein the power supply is selected from a group consisting of an Alternating Current (AC) source, a Direct Current (DC) source, a battery and a solar power source; and switch;

wherein the power supply along with the switch is connected to the signal inverting circuit and the FM transmitter to supply power during an entire process of generating and transmitting the inverted signal noise.

2. The apparatus according to claim 1, wherein the signal Output device outputs the output of the signal inverting circuit signal received by the means for receiving to cancel the undesirable signal and wherein the output of the signal inverting circuit signal combines with the noise signal to cancel or reduce or eliminate the undesirable signal.

3. The apparatus according to claim 1, wherein the sensor or the receiver has a feature for adjusting the volume of the specific signal for achieving any desired degree of noise cancellation.

4. The apparatus according to claim 1, wherein the undesirable signal is a signal selected from a group consisting of noise, and undesirable sounds.

5. The apparatus according to claim 1, wherein the means for communications is a wired network to communicate the output of the signal inverting circuit, which is transmitted using the means for transmitting.

6. The apparatus according to claim 1, wherein the means for communications is a wireless network to communicate the output of the signal inverting circuit, which is transmitted using the means for transmitting.

7. A method for cancelling signal noise comprises:

capturing undesirable signals, wherein the undesirable signals are captured using a sensor or receiver and wherein the sensor or receiver is automatically tuned to the frequency of the undesirable signal, and wherein the sensor or the receiver adjusts a volume of the undesirable signal for achieving any desired degree of noise cancellation;

generating an inverse signal of the captured undesirable signal by passing the captured undesirable signal through a signal inverting circuit, wherein the inverse of the captured undesirable signal has an amplitude which is amplitude of inverse captured, undesired signal and a frequency which is same as the frequency of the captured, undesirable signal;

transmitting the generated inverse of the captured undesirable signal through a partially wired and partially wireless network and wherein the transmitted inverse of the captured undesirable signal is communicated through an optical communication network;

communicating the transmitted signal;

receiving the transmitted inverse of the captured undesirable signal;

and outputting the received inverse of the captured undesirable signal to cancel the undesirable signal and wherein the signal noise is cancelled by replicating or mirroring a signal so that a listener is unaware of the undesirable signal and is able to focus on a desired signal.

8. The method according to claim 7, wherein the undesirable signal is a signal selected from a group consisting of noise, and undesirable sounds.

9. The method according to claim 7, wherein the transmitted inverse of the captured undesirable signal is communicated through a wired network.

10. The method according to claim 7, wherein the transmitted inverse of the captured undesirable signal is communicated through a wireless network.

* * * * *